(12) United States Patent
Mani et al.

(10) Patent No.: US 6,199,424 B1
(45) Date of Patent: Mar. 13, 2001

(54) PORTABLE UNIVERSAL FRICTION TESTING MACHINE AND METHOD

(75) Inventors: Neel K. Mani, Stow; Stanley J. Olesky; David C. Christy, both of Akron, all of OH (US)

(73) Assignee: Bridgestone/Firestone, Inc., Akron, OH (US)

( * ) Notice: Subject to any disclaimer, the term of this patent is extended or adjusted under 35 U.S.C. 154(b) by 0 days.

(21) Appl. No.: 09/276,898

(22) Filed: Mar. 25, 1999

Related U.S. Application Data (62) Division of application No. 08/835,340, filed on Apr. 7, 1997, now Pat. No. 5,900,531.

(51) Int. Cl.⁷ .................................................. G01N 19/02
(52) U.S. Cl. ........................................................... 73/9
(58) Field of Search ........................................ 73/7, 9, 10

(56) References Cited

U.S. PATENT DOCUMENTS

| | | |
|---|---|---|
| 1,534,014 | 4/1925 | Gillett . |
| 2,100,332 | 11/1937 | Hathaway et al. . |
| 2,225,140 | 12/1940 | Walker . |
| 3,033,019 | 5/1962 | Oliver . |
| 3,376,730 * | 4/1968 | Webb ........................................ 73/9 |
| 3,717,025 | 2/1973 | Kronenberg et al. . |
| 3,929,001 | 12/1975 | Lee et al. . |
| 3,948,080 | 4/1976 | Boyd . |
| 3,977,231 | 8/1976 | Haehner et al. . |
| 4,051,713 * | 10/1977 | Bao et al. .................................. 73/9 |
| 4,569,222 | 2/1986 | Arnold et al. . |
| 4,594,878 | 6/1986 | Abe et al. . |
| 4,895,015 * | 1/1990 | English ..................................... 73/9 |
| 5,097,696 | 3/1992 | Le Compagnon . |
| 5,107,448 | 4/1992 | Nash . |
| 5,113,688 | 5/1992 | Lazeration . |
| 5,167,148 | 12/1992 | Black et al. . |
| 5,212,657 | 5/1993 | Uchikawa et al. . |
| 5,245,856 * | 9/1993 | Pazzaglia et al. ........................ 73/9 |
| 5,281,535 | 1/1994 | Wei et al. . |
| 5,490,410 * | 2/1996 | Markstrom ............................... 73/9 |
| 5,501,097 | 3/1996 | Nomura . |
| 5,736,630 * | 4/1998 | Welner ..................................... 73/9 |

FOREIGN PATENT DOCUMENTS

| | | |
|---|---|---|
| 40 15 527 | 11/1991 | (DE) . |
| 0 453 703 A2 | 10/1991 | (EP) . |
| 0201138 | 8/1990 | (JP) . |
| 1601560 * | 10/1990 | (SU) ........................................ 73/9 |

OTHER PUBLICATIONS

European Search Report, EP 98104995.0.

* cited by examiner

*Primary Examiner*—Robert Raevis
(74) *Attorney, Agent, or Firm*—Thomas R. Kingsbury (57) ABSTRACT

A friction testing machine and method for measuring friction characteristics between a test sample and a friction surface. The machine and method are particularly suited for measuring the coefficient of friction between a rubber specimen or a tread element and different friction surfaces at different sliding velocities, contact pressures and orientations. A preferred embodiment of machine is self-contained and portable, configured for easy and quick changing of the friction surface, and provides for rotating the test sample about an axis normal to the sliding surface and the direction of movement of the sample relative to the friction surface. In general, a friction test machine according to the invention comprises a sample holder configured to hold a sample in frictional engagement with a friction surface, and a motion device for effecting relative movement between the friction surface and sample holder in a first direction. Also provided is a variable weight loading device on the sample holder for loading the sample holder such that a selected load can be applied to the sample normal to the friction surface, and a force measurement device for obtaining a measurement indicative of the frictional force resisting such relative movement between the sample holder and the friction surface effected by the motion device.

11 Claims, 4 Drawing Sheets

PORTABLE UNIVERSAL FRICTION TESTING MACHINE AND METHOD

This application is a divisional of Ser. No. 08/835,340 filed Apr. 7, 1997, now U.S. Pat. No. 5,900,531.

The invention herein described relates generally to friction test machines and methods and, more particularly, to a friction testing machine and method for measuring the coefficient of friction between a rubber specimen or a tread element and different friction surfaces at different speeds, contact pressures and orientations.

BACKGROUND OF THE INVENTION

When developing new compounds for tires, a prior practice was to build a tire and subject the tire to various traction tests. Because of the cost and time needed to build test tires for the purpose of optimizing traction properties, small samples of tread compounds have instead been used to determine the traction characteristics of the compounds. By using small samples for testing, a large number of different tread compounds can be made in small batches for screening to determine which compound has the best properties. The small samples could also be tested with different friction test surfaces representing different road surfaces and different conditions, whereby the traction properties of the compounds may be observed to determine which compound has the best traction on a specific road surface under specific conditions.

In U.S. Pat. No. 5,113,688 there is disclosed an apparatus and method for predicting tire traction characteristics of tread compounds using small test samples. The apparatus causes a rotating relationship between the sample and friction surface. The peak torque between the sample and friction surface is measured and a torque versus time curve is established for the sample. Such apparatus, however, does not appear to be easily movable as may be desired for testing at different locations, nor is such apparatus suitable for evaluating the performance of different tread patterns. It would be advantageous to have a portable friction testing apparatus that not only can measure the coefficient of friction of plain tread elements, but also can measure the coefficient of friction of tread blocks, shoulders, etc., of existing tires. A further desirable advantage would be an apparatus that permits one to view the interaction between the friction surface and the specimen in the same way as the present invention.

SUMMARY OF THE INVENTION

The present invention provides a friction testing machine and method for measuring friction characteristics between a test sample and a friction surface. The machine and method are particularly suited for measuring the coefficient of friction between a rubber specimen or a tread element and different friction surfaces at different sliding velocities, contact pressures and orientations. A preferred embodiment of machine is self-contained and portable, configured for easy and quick changing of the friction surface, and provides for rotating the test sample about an axis normal to the sliding surface and the direction of movement of the sample relative to the friction surface.

In general, a friction test machine according to the invention comprises a sample holder configured to hold a sample in frictional engagement with a friction surface, and a motion device for effecting relative movement between the friction surface and sample holder in a first direction. Also provided is a variable weight loading device on the sample holder for loading the sample holder such that a selected load can be applied to the sample normal to the friction surface, and a force measurement device for obtaining a measurement indicative of the frictional force resisting such relative movement between the sample holder and the friction surface effected by the motion device. Preferably, there is provided a second motion device for effecting relative movement between the sample holder and friction surface in another direction different than the first direction, such as rotation about an axis perpendicular to the friction surface and/or translation in a direction transverse to the primary direction of movement.

In one embodiment of friction test machine according to the invention, there is provided a base on which the friction surface is supported, and a carriage mounted on the base and guided for movement in a first direction parallel to the friction surface. The motion device is connected between the carriage and base for moving the carriage in the first direction, and the sample holder is mounted to the carriage for movement therewith and configured to hold the sample in frictional engagement with the friction surface during movement of the carriage in the first direction. Preferably, the friction surface is provided on a friction element, and the friction element is removably supported on the base, whereby the friction element can be interchanged with other friction elements for providing respective different friction surfaces. In a preferred embodiment, the base includes a recess for removably holding the friction element, and the base is supported on a cart for easy transport of the machine from place to place.

In another embodiment of friction testing machine according to the invention, there is provided a carriage fixed to the base, and the sample holder is mounted in the carriage for vertical movement perpendicular to the friction surface. A table is mounted to the base for rotation about a vertical axis, and the friction surface extends annularly around a radially outer peripheral portion of the table, whereby the friction surface is moved while the sample remains stationary.

In still another embodiment of friction testing machine according to the invention, there is provided a base adapted to rest on a surface against which a sample is to be tested, such as a road surface. A carriage is mounted on the base and guided for movement in a first direction parallel to the friction surface. A motion device is connected between the carriage and base for moving the carriage in the first direction, and a sample holder is mounted to the carriage for movement therewith and configured to hold the sample in frictional engagement with the friction surface during movement of the carriage in the first direction. preferably, the base is provided with an aperture through which the sample holder extends for positioning the sample against the friction surface disposed beneath the base.

In a preferred embodiment of the invention, the variable weight loading device incudes a weight platform on which removable weights can be stacked and removed to selectively vary the load applied to the sample. It also is preferred to provide the friction surface on a friction element that is easily and quickly interchangeable with other friction elements for providing respective different friction surfaces.

According to another specific aspect of the invention, there is provided a method of predicting tire traction characteristics of a tread component. The method comprises the steps of: preparing a sample of the tread component; attaching the sample to a sample holder in a friction test machine further including a motion device for effecting relative movement between a friction surface and the sample holder in a first direction; placing one or more weights on the sample holder for loading the sample holder such that a selected load can be applied to the sample normal to the friction surface; and using a force measurement device for obtaining a measurement indicative of the frictional force resisting such relative movement between the sample holder and the friction surface effected by the motion device. According to one specific methodology, the friction surface is replaceable with different friction surfaces for predicting tire traction characteristics with respect to different road surfaces.

The foregoing and other features of the invention are hereinafter fully described and particularly pointed out in the claims, the following description and the annexed drawings setting forth in detail one or more illustrative embodiments of the invention, such being indicative, however, of but one or a few of the various ways in which the principles of the invention may be employed.

DETAILED DESCRIPTION OF THE INVENTION

Figure 1:
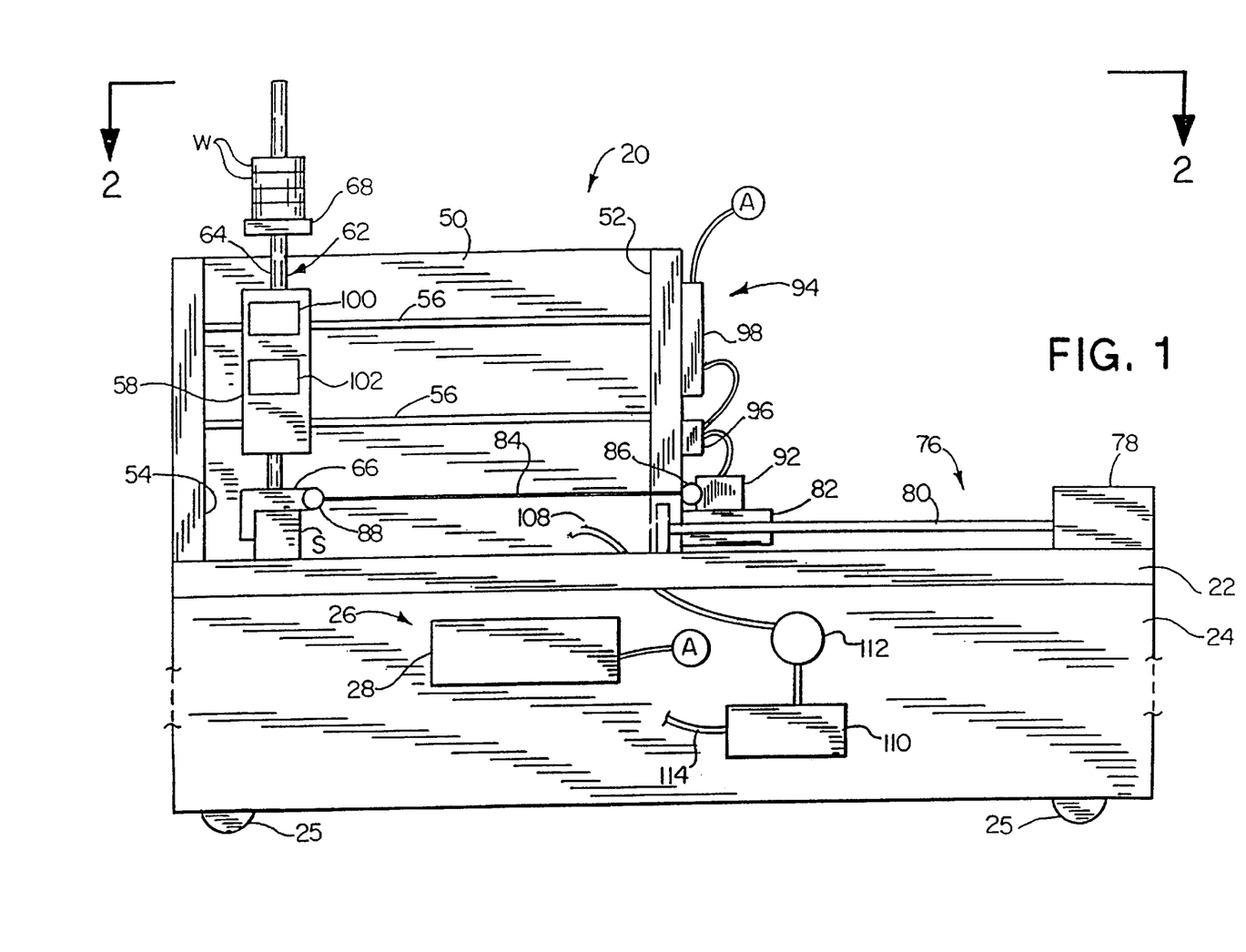
FIG. 1 is a schematic side elevational view of a portable friction testing machine according to the invention.
Figure 2:
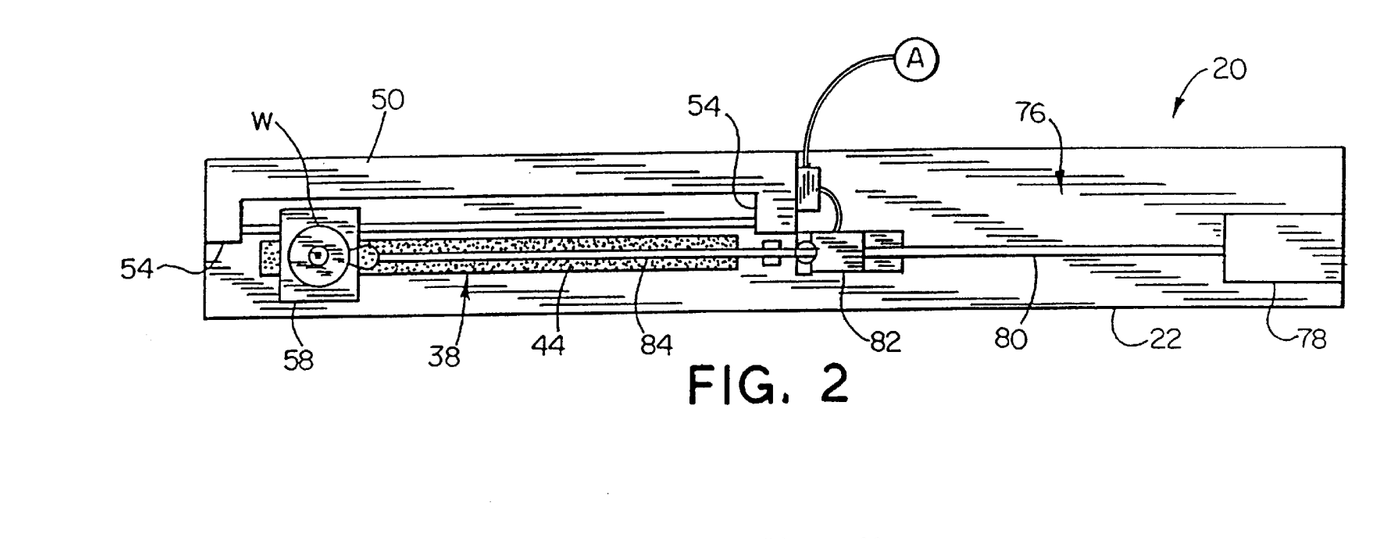
FIG. 2 is a schematic plan view of the portable friction testing machine of FIG. 1.
Figure 3:
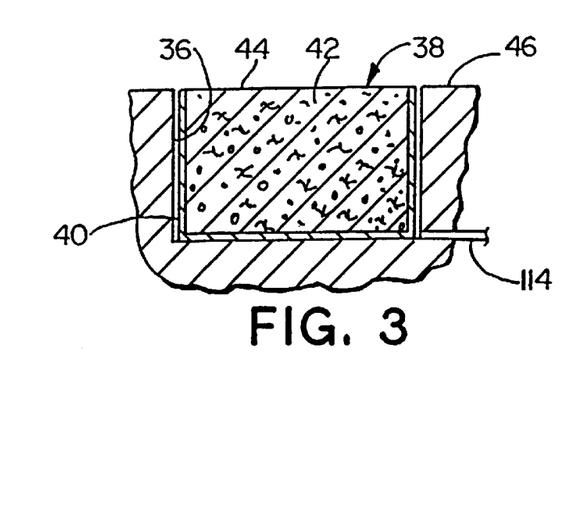
FIG. 3 is a partial sectional view taken along the line 3—3 of FIG. 1 showing details of a representative friction block used in the machine.

Referring now in detail to the drawings and initially to the embodiment of the invention shown in FIGS. 1–3, a portable friction testing machine according to the invention is schematically shown at 20. The machine 20 comprises a base 22 in the form of a plate. In the embodiment illustrated in FIGS. 1–3, the base 22 has a length several times longer than its width and is supported atop a cart 24 that may be equipped with wheels, such as casters 25, for easy transport from one place to another. As diagrammatically shown, the cart 24 also carries, for transport with the other components of the machine 22, electronic components 26 including a processor 28. The processor 28 can be a conventional microcomputer suitably programmed to carry out the various control and processing functions of the machine. As will be appreciated, the machine may be otherwise supported and configured, preferably for easy portability. For example, the machine alternatively may be supported on a table top and the base may be equipped with handles for convenient lifting of machine for transport from one table to another.

As best seen in FIG. 3, the base 22 includes a recess 36 for receiving a friction element in the form of a block 38. The friction block 38 includes a holder 40 for containing a friction material 42 that has an exposed top or friction surface 44. The holder 40 and recess 36 are correspondingly sized and configured to prevent any significant horizontal shifting of the holder relative to the platform while permitting easy removal of the friction block from the base as by lifting the friction block out of the recess in the base. This enables easy and quick interchanging of different friction blocks having different friction surfaces, as may be desired for testing a particular sample on different friction surfaces. The friction surfaces can be composed of different materials and/or textures. As will be appreciated, the friction block may be entirely formed of a single material in which case the holder and friction material are integral with one another. Preferably, the friction surface 44 is planar and flush with the top surface 46 of the base 22 and extends parallel to the longitudinal axis of the base 22 about approximately half the length of the base. Like the base, the friction surface has a length several times longer than its width.

The friction surface 44 may be any one of a variety of different surfaces. The surface may be composed of asphalt, concrete, snow, etc. and the surface may have different textures, for example rough, smooth, grooved, etc. If desired, the friction surface may have different characteristics along the length thereof, as is desirable for measuring friction characteristics of the sample as it transitions from one surface to another. For example, the first half of the friction surface may be composed of asphalt and the second half may be composed of concrete. The friction block can also be transparent to enable viewing of the sample as it moves across the friction surface. For example, the friction block can be made of glass or plexiglass having a friction surface formed by texturing, by a wire mesh on top of the glass or plexiglass substrate, etc. A camera, particularly a high speed camera, can be mounted beneath the friction block to view and record the dynamic action of the sample as it moves across the friction surface.

The base 22 has mounted thereon a vertical support plate 50 which, in the illustrated embodiment, extends approximately half the length of the base 22. The vertical support plate 50 has at opposite ends thereof in-turned mounting arms 52 and 54. Connected to and extending between the mounting arms are a pair of guides 56 in the form of rods on which a carriage 58 is mounted and guided for movement along the length of the friction surface. The carriage preferably is equipped with suitable bearings for relatively friction-free sliding on the guide rods.

The carriage 58 carries a sample holder 62. The sample holder 62 includes a post 64 that is guided by suitable bearings in the carriage 58 for vertical movement perpendicular to the friction surface. Attached to the lower end of the post 64 is a sample mount 66 to which a sample S can be removably attached by suitable means. Attached to the upper end of the post is a weight platform 68 on which weights W can be removably stacked to selectively vary the load applied to the sample. Preferably, the weights are donut shape or otherwise have a center hole for slipping over the upper end of the post or other projection extending upwardly from the weight platform 68 to hold the weights W on the platform as the carriage is moved. However, other means may be employed to hold the weights in place while still permitting easy assembly or removal of the weights on or from the platform. The amount of weight set on the platform 68 determines the amount of normal force holding the sample against the friction surface 44 as the sample is moved over the friction surface.

Movement of the sample S over the friction surface 44 is effected by a motion device 76. In the illustrated embodiment, the motion device includes a motor 78 which rotates a lead screw 80 for linearly moving a drive carriage 82 along the longitudinal axis of the base 22. The drive carriage 82 is connected to the specimen holder 66 or carriage 58 by a connecting member 84 for moving the specimen holder along with the drive carriage. In the illustrated embodiment, the connecting member 84 is a rod connected by a ball joint 86 at one end to the drive carriage and by a ball joint 88 at its opposite end to the specimen holder 66. The ball joints 86 and 88 accommodate slight misalignments between the specimen holder/carriage path and the drive carriage path. The drive motor 78 can be operated in either direction for moving the specimen holder over the friction surface in opposite directions. Moreover, the drive motor can be operated at different speeds to provide a large range of sliding velocities. For example, when measuring the coefficient of friction of a tread compound, the motor can be operated at sliding velocities comparable to what a tire experiences in service. For example, translation speeds in the range of zero to about 4.0 inches/second can be obtained. As will be appreciated, other connecting members can be used, such as a wire to pull the specimen holder/carriage in one direction over the friction surface.

The drive carriage 82 has secured thereto a force measurement device 92, such as a load cell, which measures the horizontal force at the footprint of the sample. It is the load cell 92 to which the connecting rod 84 is connected by the ball joint 86. As the drive carriage moves the sample holder 66 over the friction surface 44, the load cell will output a signal indicative of the frictional force resisting movement of the sample across the friction surface. The output of the load cell is connected to a data acquisition system 94. More particularly, the output of the load cell 92 is connected by a shunt calibrator 96 to a charge amplifier 98 which in turn is connected to the processor 28. As those skilled in the art will appreciate, the shunt calibrator is provided for easy calibration of the system. The processor 28 processes the output of the sensor to provide a measurement of the friction characteristics, e.g., coefficient of friction, of the sample S being tested for the selected friction surface.

In the case of a tread element, for example, it may be desirable to measure the coefficient of friction in different directions. To this end, the sample holder 66 can be rotated about its vertical axis (normal to the friction surface) in the carriage 58 and then fixed by suitable means at a selected angle of rotation.

For some tests, It is desirable to give the sample two independent translations in two orthogonal directions, a translation and rotation, or both. The linear movement of the sample S across the friction surface effected by the motor 78 constitutes translation in one orthogonal direction. To obtain translation in a second orthogonal direction, there is provided a transverse drive mechanism 100 for moving the sample holder transversely back and forth relative to the linear movement direction of the carriage. To obtain rotation about an axis perpendicular to the friction surface, a rotation mechanism 102 is provided for rotating the sample holder during movement of the sample linearly across the friction surface. Preferably, the transverse drive mechanism 100 and rotation mechanism 102 are housed in the carriage 58, as diagrammatically depicted in FIG. 1, and operate on the post 64 for effecting transverse and rotational movement of the sample holder 66. For example, the rotation mechanism 102 can be a motor and suitable gearing and/or other drive components for rotating the sample holder in a controlled manner. For some tests, it may be desirable to reciprocally rotate the sample back and forth as it is moved along the friction surface. Similarly, the transverse drive mechanism 100 can be a motor and suitable gearing and/or other drive components for moving the sample holder transversely to the direction of movement of the carriage along the length of the friction surface. If the sample holder 66 is undergoing rotational or transverse movement during testing, then preferably the connecting member 84 is connected to the carriage 58, and thus indirectly to the sample holder instead of directly to the sample holder 66.

Tests can also be conducted under wet conditions. To this end, water can be applied to the friction surface 44 by a tube 108 connected to a reservoir 110 or other source of water. In the illustrated embodiment, a pump 112 is used to pump the water onto the friction surface 44 at a desired rate or when needed. A suitable drain 114 (FIG. 3) is preferably provided, for example at the bottom of the recess 36 in the base 22, for removing water from the test area and, if desired, recycling the water back to the reservoir 110 as shown in FIG. 1. For wet tests, the friction block preferably is provided with suitable drain passages, as along the edges thereof for channeling the water to the drain, as opposed to the water flowing over the top surface of the base. However, it will be appreciated that the base alternatively or additionally may be configured for collection of the water being applied to the friction surface. Also, a distribution member, such as a manifold with multiple outlets spaced along the length of the friction surface, can be employed for more even distribution of water over the friction surface.

Figure 4:
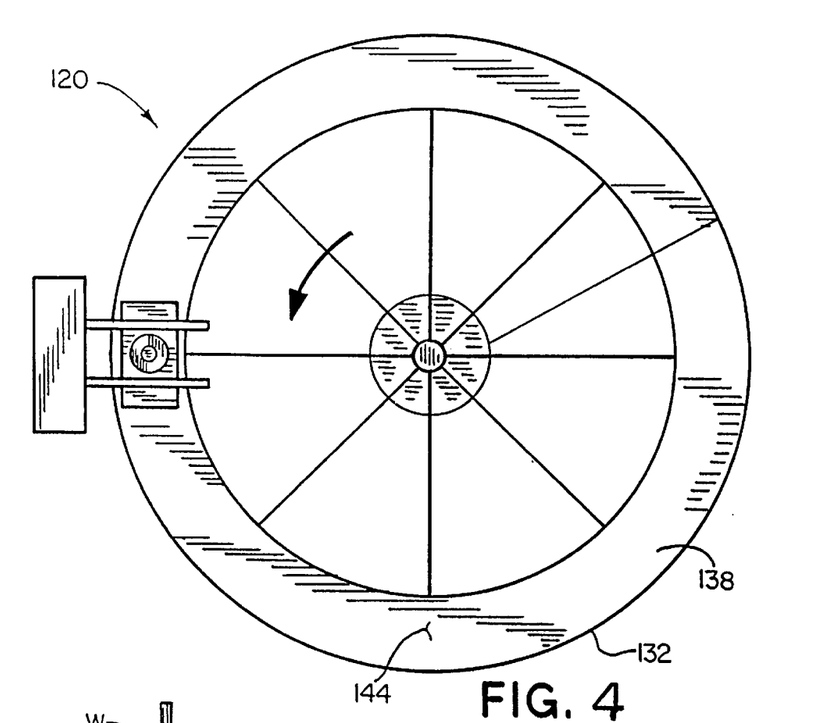
FIG. 4 is a schematic plan view of another embodiment of portable friction testing machine according to the invention.
Figure 5:
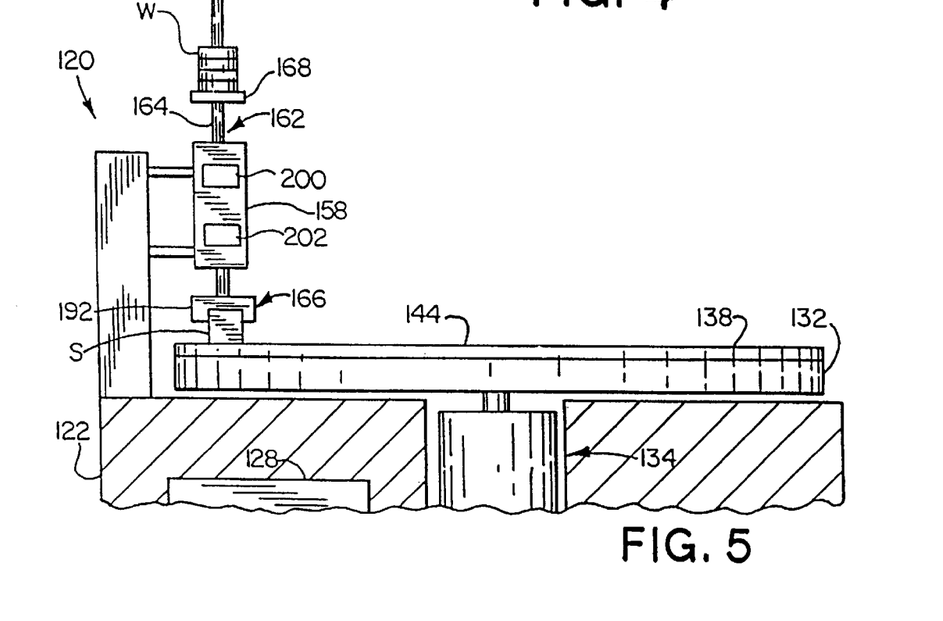
FIG. 5 is a schematic side elevational view of the portable friction testing machine of FIG. 3.

Referring now to FIGS. 4 and 5, another embodiment of portable friction testing machine according to the invention is schematically shown at 120. The machine 120 comprises a base 122 supported on or in the form of a cart 124 that may be equipped with wheels, such as casters, for easy transport from one place to another. Like in the above described testing machine 20, the cart 124 preferably carries, for transport with the other components of the machine 122, electronic components 126 including a processor 128. As before, the processor 128 can be a conventional microcomputer suitably programmed to carry out the various control and processing functions of the machine.

The base 122 has mounted thereon a table 132 that rotates about a vertical axis. The table is driven by a motion device 134 including, for example, a motor 136 and suitable controls for controlling the speed of the motor. The outer peripheral annular edge portion of the table is covered by a friction surface preferably provided by a removable annular friction element 138. The removable friction element 138 is in the form of an annular disc-like holder for containing a friction material that has an exposed annular top or friction surface 144. The annular friction element 138 is concentric with the rotation axis of the rotating table 132 and is suitably secured to the rotating table by suitable means for rotation therewith. Preferably, the friction element is removably secured for permitting easy and quick interchanging of different friction elements having different friction surfaces, as may be desired for testing a particular sample on different friction surfaces. As before, the surfaces can be composed of different materials and/or textures, such as those above mentioned.

The base 122 has mounted thereon a carriage 158 located above the friction surface 144 on the rotating table 132. The carriage 158 has mounted therein a sample holder 162 which includes a post 164 that is guided by suitable bearings in the carriage 158 for vertical movement perpendicular to the friction surface 144. Attached to the lower end of the post 164 is a sample mount 166 to which a sample S can be removably attached by suitable means. Attached to the upper end of the post is a weight platform 168 on which weights W can be removably stacked to selectively vary the load applied to the sample, as in the manner described above in connection with the testing machine 20. The amount of weight set on the platform 168 determines the amount of normal force holding the sample against the friction surface as the sample is moved over the friction surface.

As will be appreciated, movement of the sample S relative to the friction surface 144 is effected by rotating the table 132. The drive motor 136 can be operated in either direction for moving the friction surface relative to the sample in opposite directions. Moreover, the drive motor can be operated at different speeds to provide a large range of sliding velocities, such as the above mentioned range. The rotating table preferably is of a sufficiently large diameter that the sample in essence is moving linearly relative to the friction surface, this essentially being equivalent to the linear translating movement of the sample in the testing machine 20.

The sample mount 166 includes a force measurement device 192, such as a load cell, which measures the horizontal force at the footprint of the sample S parallel to the movement direction of the sample relative to the friction surface 144. As the motor 136 moves the friction surface 144 underneath the sample holder 158, the load cell 192 will output a signal indicative of the frictional force resisting movement of the sample across the friction surface. The output of the load cell is connected to a data acquisition system as above described.

As above indicated, it may be desirable to measure the coefficient of friction in different directions. To this end, the sample holder 166 can be rotated about its vertical axis (normal to the friction surface) in the carriage 158 and then fixed by suitable means at a selected angle of rotation.

Again, for some tests, It is desirable to give the sample two independent translations in two orthogonal directions, a translation and rotation, or both. The movement of the rotating friction surface 144 beneath the sample S essentially constitutes translation in one orthogonal direction. To obtain translation in a second orthogonal direction, a transverse drive mechanism 200 for moving the sample holder transversely back and forth relative to the linear movement direction of the carriage. To obtain rotation about an axis perpendicular to the friction surface, a rotation mechanism 202 is provided for rotating the sample holder relative to the carriage while the friction surface is moving beneath the sample. Preferably, the transverse drive mechanism 200 and rotation mechanism 202 are housed in the carriage 158 as diagrammatically depicted in FIG. 5.

Figure 6:
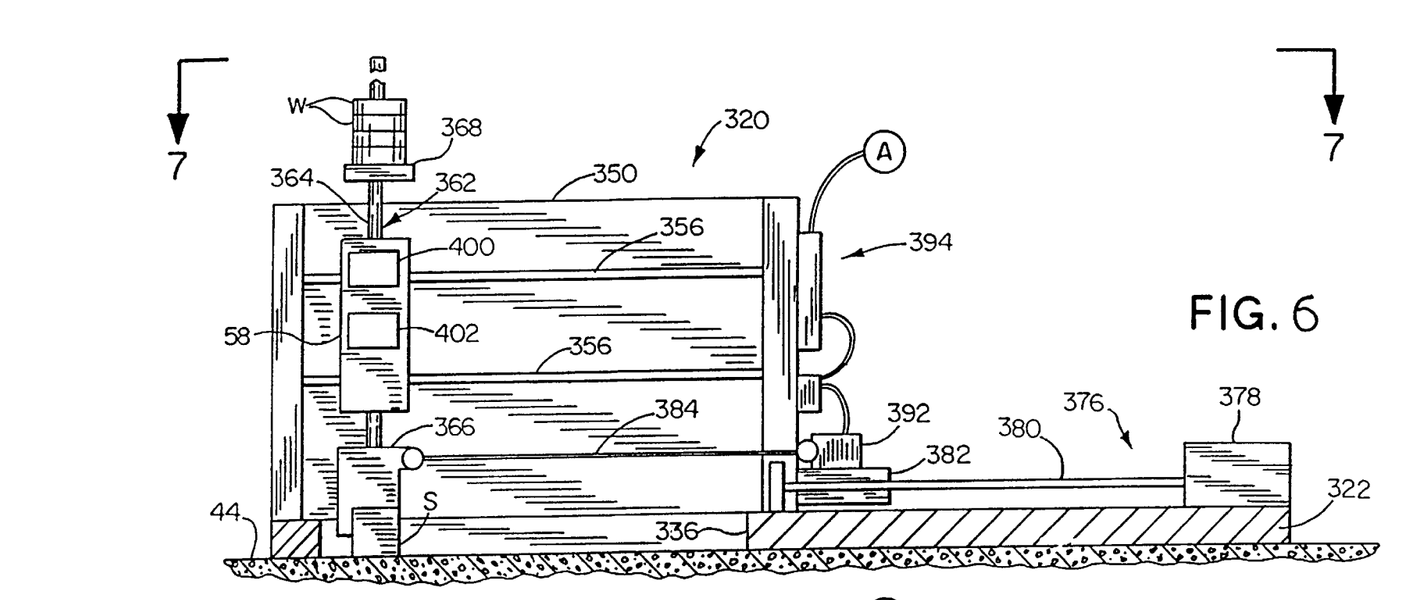
FIG. 6 is a schematic side elevational view of a further embodiment of portable friction testing machine according to the invention.
Figure 7:
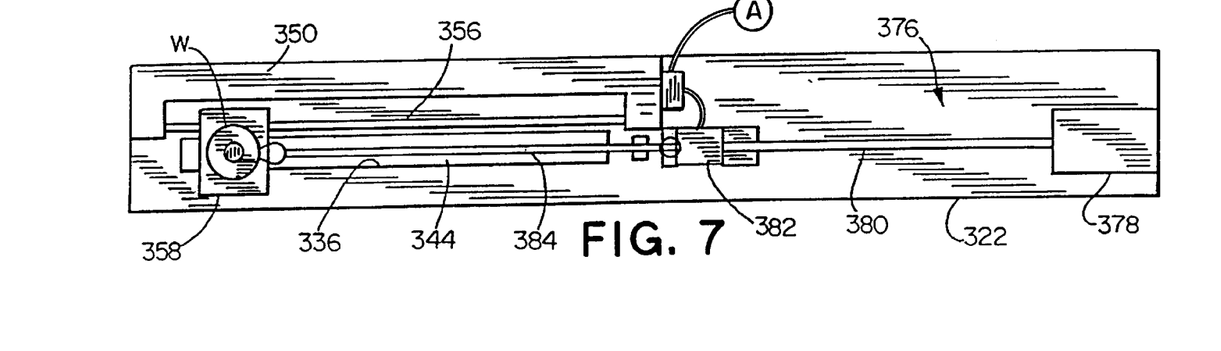
FIG. 7 is a schematic plan view of the portable friction testing machine of FIG. 6.

FIGS. 6 and 7 show a further embodiment of portable friction testing machine according to the invention. The machine 320 is substantially the same as the above described machine 20, except that it modified as discussed below to provide for in situ testing of a friction surface, such a floor surface or roadway surface. Thus, the electronic components of the machine 320 are the same as above described in connection with machine 20, although the processor is not shown in FIGS. 6 and 7.

Like the machine 20, the machine 320 comprises a base 322 in the form of a plate. The base 322 is adapted to rest atop the friction surface 344 against which a sample is to be tested. If desired, the base may be carried by a cart (not shown) that may be equipped with wheels, such as casters, for easy transport from one place to another. The cart may be equipped with a mechanism for lowering the base, when testing is desired, to a position adjacent a friction surface on which the cart is supported. As will be appreciated, the machine may be otherwise supported and configured, preferably for easy portability. For example, the machine alternatively may be equipped with handles for convenient lifting of machine for transport from one place to another.

The base 322 includes an aperture and more particularly an elongated through opening 336 for permitting access to the underlying friction surface by a sample S in a sample holder 362. The sample holder 362 includes a post 364 that is guided by suitable bearings in a carriage 358 for vertical movement perpendicular to the friction surface. Attached to the lower end of the post 364 is a sample mount 366 to which the sample S can be removably attached by suitable means. As seen in FIG. 6, the sample holder (including the sample) extends through the opening 336 in the base for engagement with the friction surface underlying the base.

The upper end of the post 364 is provided with a weight platform 368 on which weights W can be removably stacked to selectively vary the load applied to the sample. As in the case of the machine embodiment of FIGS. 1 and 2, the amount of weight set on the platform 368 determines the amount of normal force holding the sample against the friction surface as the sample is moved over the friction surface. Likewise, the base 322 has mounted thereon a vertical support plate 350. Connected to and extending between mounting arms on the support plate are a pair of guides 356 in the form of rods on which a carriage 358 is mounted and guided for movement along the length of the elongated opening 336 in the base.

Movement of the sample S over the friction surface 344 is effected by a motion device 376 including, for example, a motor 378 which rotates a lead screw 380 for linearly moving a drive carriage 382 along the longitudinal axis of the base 322. The drive carriage 382 is connected to the specimen holder 366 or carriage 358 by a connecting member 384 for moving the specimen holder along with the drive carriage. The drive motor 378 can be operated in either direction for moving the specimen holder over the friction surface in opposite directions. Moreover, the drive motor can be operated at different speeds to provide a large range of sliding velocities.

The drive carriage 382 has secured thereto a force measurement device 392, such as a load cell, which measures the horizontal force at the footprint of the sample. As the drive carriage moves the sample holder 366 over the friction surface 344, the load cell will output a signal indicative of the frictional force resisting movement of the sample across the friction surface. The output of the load cell is connected to a data acquisition system 394 as above described in connection with the machine embodiment 20 of FIGS. 1 and 2. The output of the sensor provides a measurement of the friction characteristics, e.g., coefficient of friction, of the sample S being tested for the selected friction surface. As before described, the sample holder 366 can be rotated about its vertical axis (normal to the friction surface) in the carriage 358 and then fixed by suitable means at a selected angle of rotation. Additionally or alternatively, the sample may be given two independent translations in two orthogonal directions, a translation and rotation, or both. The linear movement of the sample S across the friction surface effected by the motor 378 constitutes translation in one orthogonal direction. To obtain translation in a second orthogonal direction, there is provided a transverse drive mechanism 400 for moving the sample holder transversely back and forth relative to the linear movement direction of the carriage. To obtain rotation about an axis perpendicular to the friction surface, a rotation mechanism 402 is provided for rotating the sample holder during movement of the sample linearly across the friction surface. Preferably, the transverse drive mechanism 400 and rotation mechanism

402 are housed in the carriage 358, as diagrammatically depicted in FIG. 6, and operate on the post 364 for effecting transverse and rotational movement of the sample holder 366.

By way of example, the aforesaid testing machines can be used predict tire traction characteristics of a tread component. First, a sample of the tread component is prepared and attached to the sample holder in either one of the above described friction test machines. Then, one or more weights can be placed on the sample holder for loading the sample holder such that a selected load is applied to the sample normal to the friction surface. The test machine is then operated to slide the sample over the friction surface while data is collected by the processor to provide measurements indicative of the frictional force resisting relative movement between the sample holder and the friction surface effected by the motion device. The resistance force can be used to calculate the coefficient of friction of the sample relative to the friction surface. As above discussed, the friction surface, in the first two embodiments described above, is replaceable with different friction surfaces for predicting tire traction characteristics with respect to different road surfaces. In the third embodiment above described, the testing machine can be positioned on different surfaces, such as different roadway surfaces. As will be appreciated, the testing machine can be used to determine the frictional characteristics of a sample, for example a section of an actual tire tread, in relation to a friction surface, in situ, for example a roadway surface.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function of the described integer (i.e., that is functionally equivalent), even though not structurally equivalent to the disclosed structure which performs the function in the herein illustrated exemplary embodiment or embodiments of the invention. In addition, while a particular feature of the invention may have been described above with respect to only one of several illustrated embodiments, such feature may be combined with one or more other features of the other embodiments, as may be desired and advantageous for any given or particular application.

What is claimed is:

1. A friction test machine comprising:
   a base;
   a carriage mounted on said base and guided for movement in a first direction parallel to a friction surface;
   a motion device connected between said carriage and base for moving said carriage in said first direction;
   a sample holder mounted to said carriage for movement therewith and configured to hold a sample in frictional engagement with the friction surface during movement of said carriage in said first direction;
   a variable weight loading device carried on said carriage for loading the sample holder such that a selected load can be applied to the sample normal to the friction surface;
   a force measurement device for obtaining a measurement indicative of the frictional force resisting movement of the sample as it is moved in said first direction; and
   wherein said motion device includes a motor, a screw rotated by said motor, a drive carriage operatively connected to said screw for translating movement in said first direction when said screw is rotated by said motor in a corresponding direction, and a connecting member connecting said drive carriage to said sample holder for effecting movement of said sample holder with said drive carriage;
   wherein the motor can be operated in either direction thereby moving the sample holder over the friction surface in opposite directions.

2. A friction test machine as set forth in claim 1, wherein said force measurement device includes a load cell that outputs a signal indicative of the friction force resisting movement of the sample across the frictional surface.

3. A friction test machine as set forth in claim 2 further comprising a processor which processes the output from the load cell to provide measurement of friction characteristics of the sample for the friction surface.

4. A friction test machine as set forth in claim 1, wherein said force measurement device includes a load cell mounted to said drive carriage and connected to said connecting member.

5. A friction test machine comprising:
   a carriage;
   a motion device for effecting relative movement between said carriage and a friction surface in a first direction;
   a sample holder guided by said carriage for movement in a direction perpendicular to the friction surface and said first direction, said sample holder being configured to hold a sample in frictional engagement with the friction surface during relative movement between said carriage and friction surface in said first direction;
   a variable weight loading device carried on said carriage for loading the sample holder such that a selected load can be applied to the sample normal to the friction surface, said variable weight loading device including a weight platform on which removable weights can be stacked and removed to selectively vary the load applied to the sample; and
   a force measurement device for obtaining a measurement indicative of the frictional force resisting movement of the sample as it is moved in said first direction;
   wherein said motion device includes a motor, a screw rotated by said motor, a drive carriage operatively connected to said screw for translating movement in said first direction when said screw is rotated by said motor in a corresponding direction, and a connecting member connecting said drive carriage to said sample holder for effecting movement of said sample holder with said drive carriage;
   wherein the motor can be operated in either direction thereby moving the sample holder over the friction surface in opposite directions whereby the force measurement device can obtain measurements indicative of the friction force resisting movement of the sample as the sample is moved in opposite directions.

6. A friction test machine as set forth in claim 5, wherein said force measurement device includes a load cell mounted to said drive carriage and connected to said connecting member.

7. A friction test machine as set forth in claim 5, wherein said force measurement device includes a load cell that outputs a signal indicative of the friction force resisting movement of the sample across the frictional surface.

8. A friction test machine comprising:
   a carriage;
   a motion device for effecting relative movement between said carriage and a friction surface in a first direction;

a sample holder guided by said carriage for movement in a direction perpendicular to the friction surface and said first direction, said sample holder being configured to hold a sample in frictional engagement with the friction surface during relative movement between said carriage and friction surface in said first direction;

a variable weight loading device carried on said carriage for loading the sample holder such that a selected load can be applied to the sample normal to the friction surface, said variable weight loading device including a weight platform on which removable weights can be stacked and removed to selectively vary the load applied to the sample;

a force measurement device for obtaining a measurement indicative of the frictional force resisting movement of the sample as it is moved in said first direction; and wherein said motion device includes a motor, a screw rotated by said motor, a drive carriage operatively connected to said screw for translating movement in said first direction when said screw is rotated by said motor in a corresponding direction, and a connecting member connecting said drive carriage to said sample holder for effecting movement of said sample holder with said drive carriage;

wherein said force measurement device includes a load cell that outputs a signal indicative of the friction force resisting movement of the sample across the frictional surface; and wherein the friction test machine further comprises a processor which processes the output from the load cell to provide measurement of friction characteristics of the sample for the friction surface.

9. A friction test machine comprising:

a carriage;

a motion device for effecting relative movement between said carriage and a friction surface in a first linear direction;

a sample holder guided by said carriage for movement in a direction perpendicular to the friction surface and said first direction, said sample holder being configured to hold a sample in frictional engagement with the friction surface during relative movement between said carriage and friction surface in said first direction;

a variable weight loading device carried on said carriage for loading the sample holder such that a selected load can be applied to the sample normal to the friction surface, said variable weight loading device including a weight platform on which removable weights can be stacked and removed to selectively vary the load applied to the sample;

a force measurement device for obtaining a measurement indicative of the frictional force resisting movement of the sample as it is moved in said first direction; and a base adapted to rest on the friction surface against which the sample is to be tested, said base being provided with an aperture through which the sample holder extends for positioning the sample against the friction surface disposed beneath the base;

wherein the motion device can move the sample holder over the friction surface in opposite linear directions whereby the force measurement device can obtain measurements indicative of the friction force resisting movement of the sample as the sample is moved in the opposite linear directions.

10. A friction test machine as set forth in claim 9, wherein said force measurement device includes a load cell that outputs a signal indicative of the friction force resisting movement of the sample across the frictional surface.

11. A friction test machine as set forth in claim 10, further comprising a processor which processes the output from the load cell to provide measurement of friction characteristics of the sample for the friction surface.

\* \* \* \* \*